(12) United States Patent
Ries et al.

(10) Patent No.: US 10,154,834 B2
(45) Date of Patent: Dec. 18, 2018

(54) SURGICAL TOOL DEVICE

(71) Applicant: JOIMAX GMBH, Karlsruhe (DE)

(72) Inventors: Wolfgang Ries, Linkenheim (DE);
Achim Krausemann, Karlsruhe (DE)

(73) Assignee: JOIMAX GMBH, Karslruhe (DE)

( * ) Notice: Subject to any disclaimer, the term of this patent is extended or adjusted under 35 U.S.C. 154(b) by 221 days.

(21) Appl. No.: 15/137,266

(22) Filed: Apr. 25, 2016

(65) Prior Publication Data

US 2016/0235416 A1    Aug. 18, 2016

Related U.S. Application Data

(62) Division of application No. 14/347,371, filed as application No. PCT/EP2013/001151 on Apr. 18, 2013, now Pat. No. 9,439,634.

(30) Foreign Application Priority Data

May 3, 2012    (DE) ........................ 10 2012 008 970

(51) Int. Cl.
  *A61B 1/00*     (2006.01)
  *A61B 17/00*    (2006.01)
  *A61B 1/313*    (2006.01)
  *A61B 17/16*    (2006.01)
  *A61B 17/32*    (2006.01)
  *A61B 1/012*    (2006.01)

(52) U.S. Cl.
  CPC .... *A61B 17/00234* (2013.01); *A61B 1/00128* (2013.01); *A61B 1/012* (2013.01); *A61B 1/3135* (2013.01); *A61B 17/1615* (2013.01); *A61B 17/1637* (2013.01); *A61B 17/1671* (2013.01); *A61B 17/32002* (2013.01); *A61B 2017/00261* (2013.01); *A61B 2017/00331* (2013.01); *A61B 2017/1602* (2013.01); *A61B 2217/005* (2013.01); *A61B 2217/007* (2013.01)

(58) Field of Classification Search
  CPC . A61B 17/1637; A61B 1/00128; A61B 1/012; A61B 1/3135; A61B 2017/00261; A61B 2017/00331
  USPC ................ 600/106, 104, 137; 604/528, 921; 606/206, 208
  See application file for complete search history.

(56) References Cited

U.S. PATENT DOCUMENTS 1,880,551 A * 10/1932 Wappler ............. A61B 1/00105
                                          600/104
3,784,235 A *  1/1974 Kessler ............... B29C 65/5057
                                          156/294

(Continued)

*Primary Examiner* — Timothy J Neal
*Assistant Examiner* — Jae Woo
(74) *Attorney, Agent, or Firm* — McGlew and Tuttle, P.C.

(57) ABSTRACT

When processing bone tissue, the work site is often out of alignment with the insertion path of a tool device. A tool device (1) is provided with an endoscope (2), through the working channel (2.1) of which a guiding part (3) and a tool part (5) guided in this can be moved with their distal ends to a distal working area. The tool part (5) has a tool shaft (5.1) with a rotating tool (5.3). In the tool device there is a secure connection between the endoscope and the guiding part, during the task, and, this connection can be established in a simple manner prior to the beginning of the task and it can also be released again in a simple manner after the task ends. The guiding part (3) is able to be connected rigidly with the endoscope (2) axially.

21 Claims, 7 Drawing Sheets

(56) References Cited

U.S. PATENT DOCUMENTS

| | | | | | |
|---|---|---|---|---|---|
| 3,909,045 | A * | 9/1975 | Meagher | F16L 13/11 | 285/22 |
| 4,202,184 | A * | 5/1980 | Krude | F16D 1/072 | 285/382 |
| 4,323,304 | A * | 4/1982 | Ishii | A61B 1/00128 | 396/17 |
| 4,328,593 | A * | 5/1982 | Sutter | A61F 2/3603 | 623/23.42 |
| 4,513,488 | A * | 4/1985 | Arena | B21D 26/14 | 285/382.2 |
| 4,621,481 | A * | 11/1986 | Magnusson | B67B 3/14 | 53/345 |
| 4,782,819 | A * | 11/1988 | Adair | A61B 1/042 | 600/109 |
| 4,812,073 | A * | 3/1989 | Blumberg | B62D 7/16 | 285/256 |
| 4,832,523 | A * | 5/1989 | Glatzel | F16C 33/145 | 277/635 |
| 5,076,279 | A * | 12/1991 | Arenson | A61B 1/00142 | 600/459 |
| 5,381,787 | A * | 1/1995 | Bullard | A61B 1/0056 | 600/188 |
| 5,406,940 | A * | 4/1995 | Melzer | A61B 1/00087 | 600/106 |
| 5,417,203 | A * | 5/1995 | Tovey | A61B 17/29 | 600/106 |
| 5,437,630 | A * | 8/1995 | Daniel | A61B 17/32002 | 604/22 |
| 5,446,944 | A * | 9/1995 | Coleman | E05C 17/28 | 16/63 |
| 5,630,798 | A * | 5/1997 | Beiser | A61B 1/00135 | 604/30 |
| 5,685,853 | A * | 11/1997 | Bonnet | A61B 1/018 | 600/106 |
| 5,928,137 | A * | 7/1999 | Green | A61B 1/00052 | 600/104 |
| 6,312,438 | B1 * | 11/2001 | Adams | A61B 17/32002 | 606/159 |
| 7,507,232 | B1 * | 3/2009 | Garito | A61B 18/148 | 606/15 |
| 2003/0040753 | A1 * | 2/2003 | Daum | A61B 17/3403 | 606/96 |
| 2006/0178560 | A1 * | 8/2006 | Saadat | A61B 1/0055 | 600/114 |
| 2007/0213687 | A1 * | 9/2007 | Barlow | A61M 25/0662 | 604/523 |
| 2009/0043258 | A1 * | 2/2009 | Fujisaki | A61B 17/3478 | 604/164.01 |
| 2009/0105775 | A1 * | 4/2009 | Mitchell | A61B 17/1757 | 606/86 R |
| 2009/0198258 | A1 * | 8/2009 | Workman | A61B 17/3421 | 606/148 |
| 2011/0112359 | A1 * | 5/2011 | Mark | A61B 1/00128 | 600/104 |
| 2011/0184234 | A1 * | 7/2011 | Morgenstren Lopez | A61B 5/417 | 600/107 |
| 2012/0139236 | A1 * | 6/2012 | Novitsky | B21D 41/00 | 285/399 |
| 2012/0143206 | A1 * | 6/2012 | Wallace | A61B 17/00234 | 606/103 |

* cited by examiner

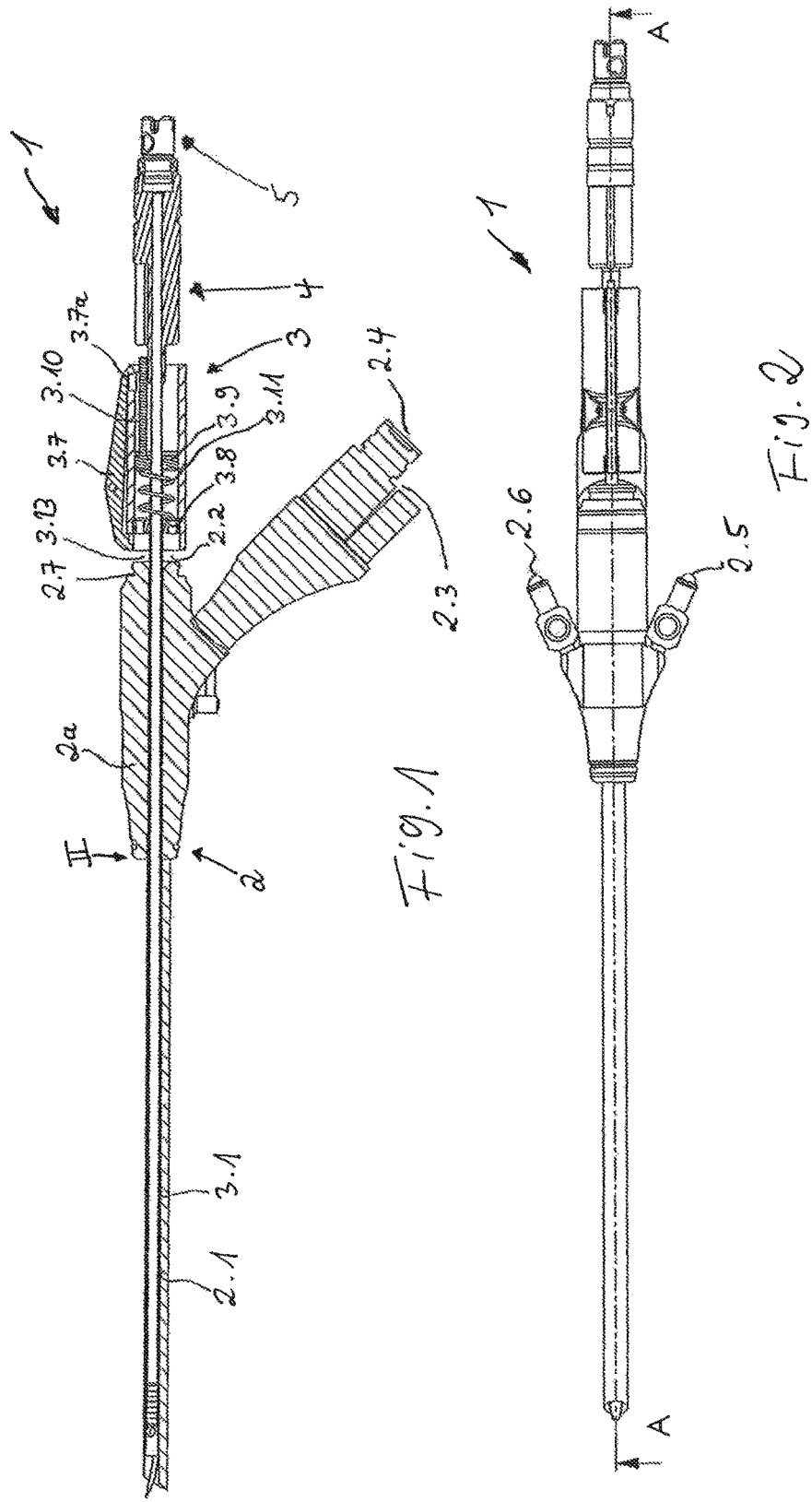

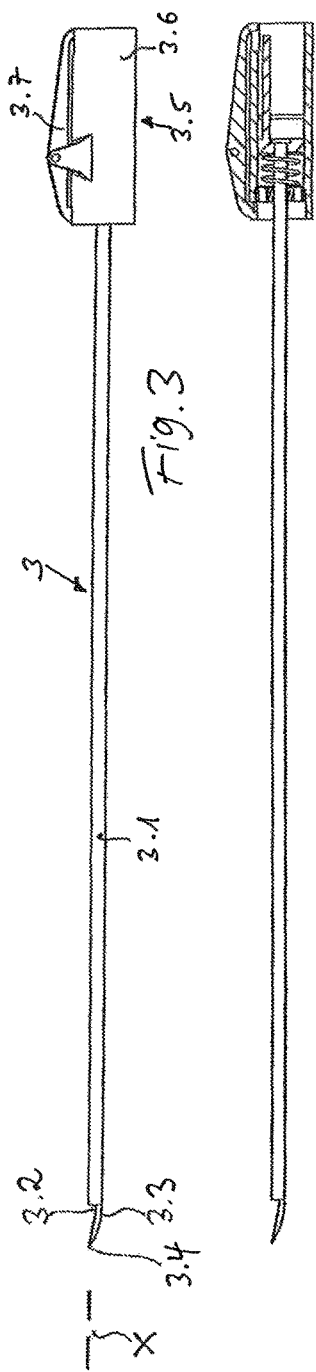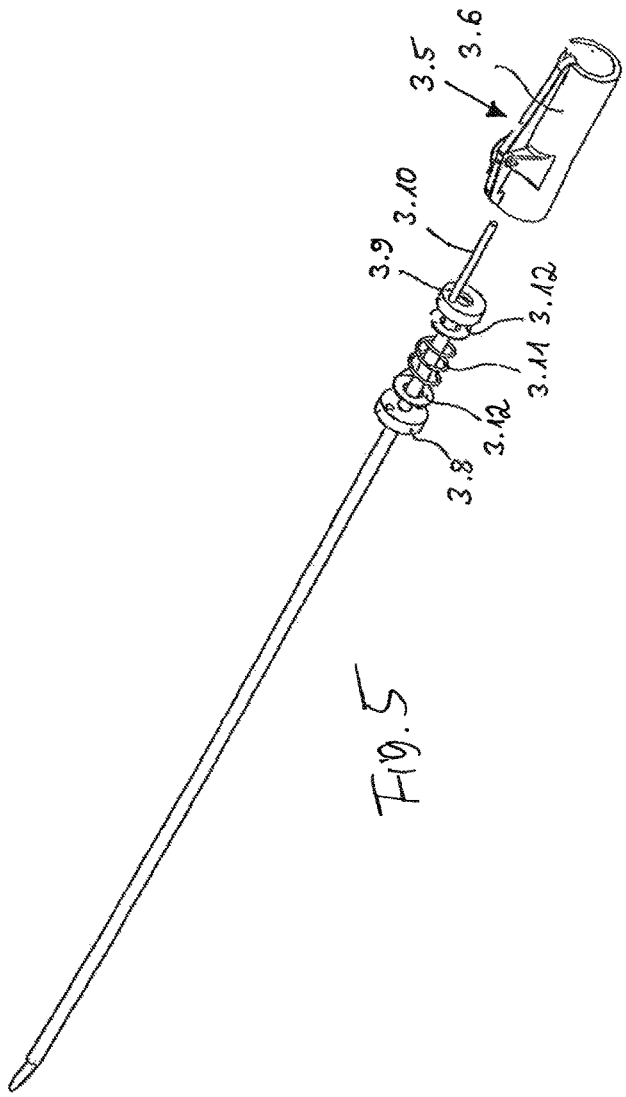
Fig. 3
Fig. 4
Fig. 5

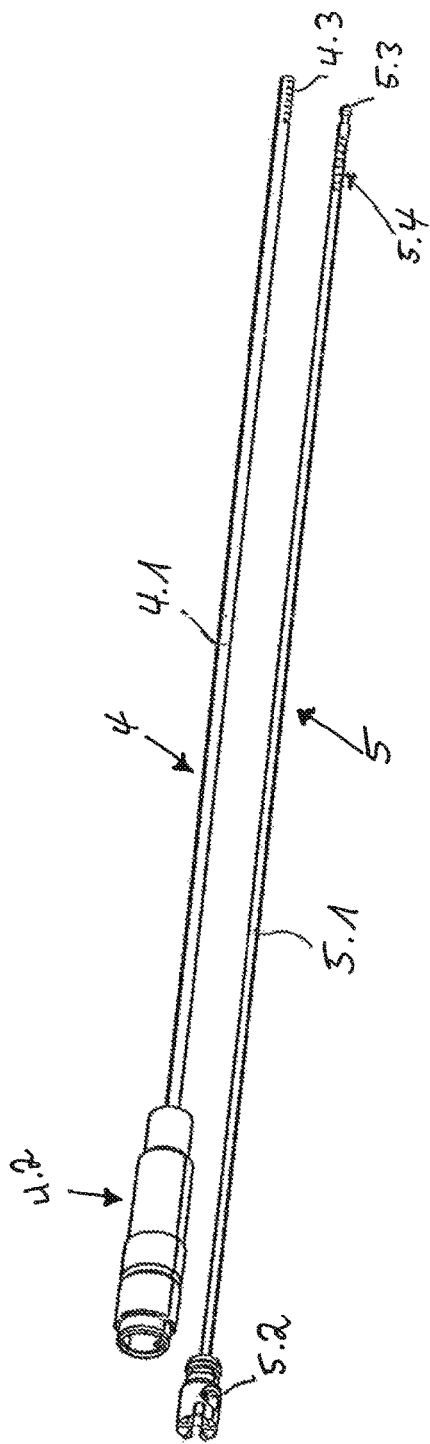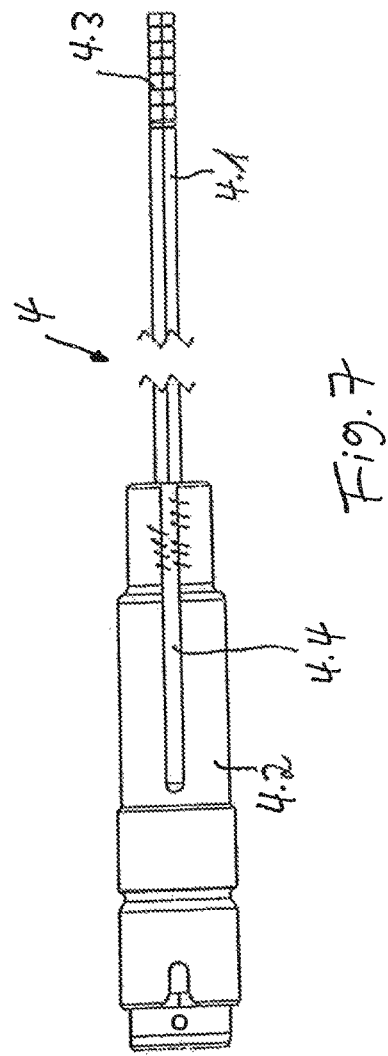
Fig. 6
Fig. 7

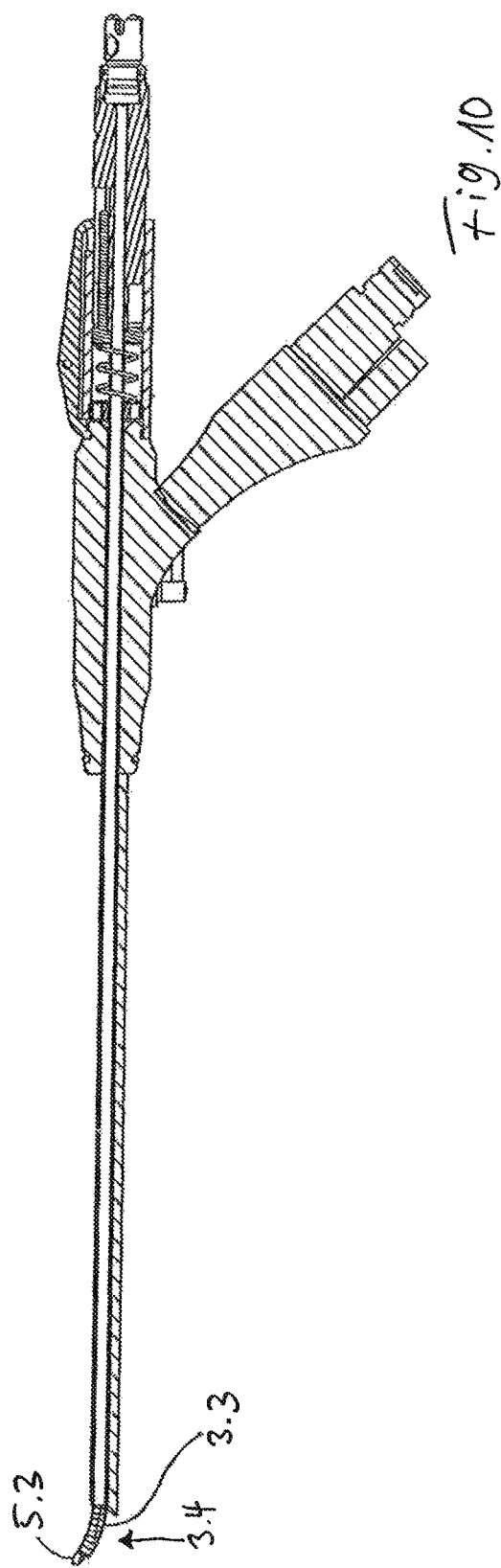

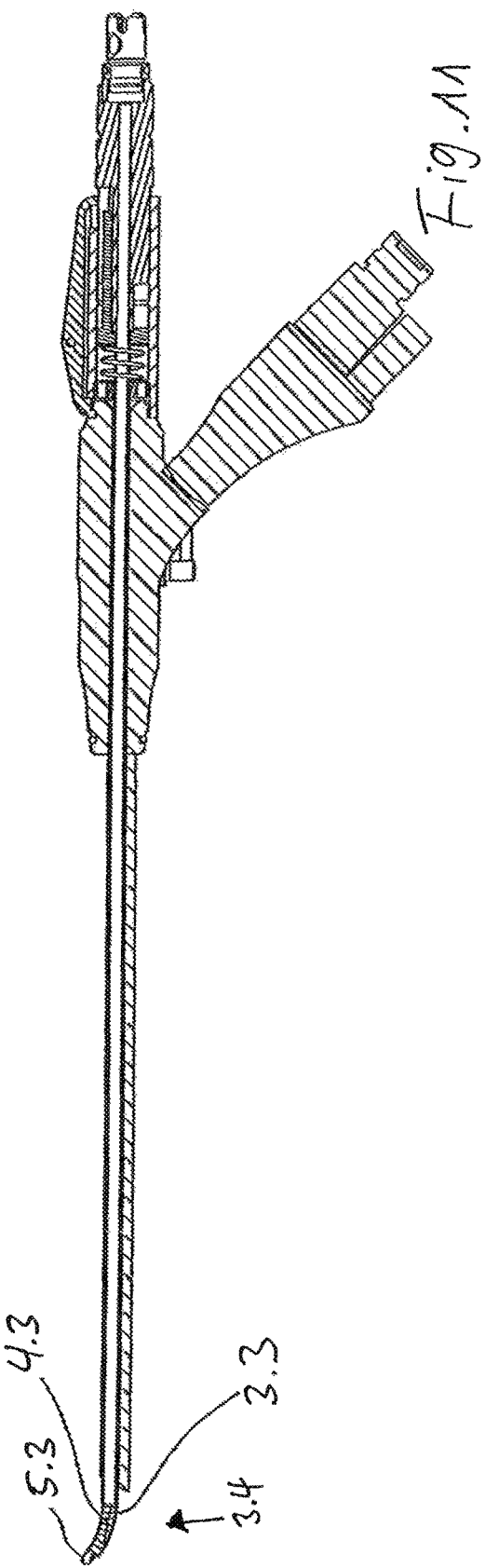

SURGICAL TOOL DEVICE

CROSS REFERENCE TO RELATED APPLICATIONS

This application is a divisional patent application of United States National Phase application Ser. No. 14/347,371 filed Mar. 26, 2014, of International Application PCT/EP2013/001151 filed Apr. 18, 2013, and claims the benefit of priority under 35 U.S.C. § 119 of DE 10 2012 008 970.8 filed May 3, 2012, the entire contents of which are incorporated herein by reference.

FIELD OF THE INVENTION

The present invention pertains to a surgical tool device, with an endoscope, through the working channel of which a guiding part and a tool part being guided therein can be moved with the distal ends thereof to a distal working area, wherein the tool part has a tool shaft with a rotary tool.

BACKGROUND OF THE INVENTION

Such surgical tool devices are used for working in tissue, especially bone tissue, such as in the region of vertebrae, for example, in order to remove tissue coming into contact with nerves there, also intervertebral disk tissue, or to create conditions for stabilization, such as the fixation of two vertebrae. The tools to be used are rotationally driven tools, such as drills or cutters. They are inserted microinvasively endoscopically. It is often very difficult or impossible to insert a tool device microinvasively endoscopically to its work site such that it is aligned with the insertion path and also with the axis of the tool device, without jeopardizing delicate organs, blood vessels or nerves over this path. It is therefore desirable or even necessary to select a working channel at the end of which the work site will be out of alignment with or is offset in relation to the working channel and the tool axis.

SUMMARY OF THE INVENTION

A basic object of the present invention is therefore to create a surgical tool device with a rotationally driven tool, which makes it possible to process tissue, especially also bone tissue, outside the alignment of the axis of the tool or of the insertion path. Flexibility shall now be ensured to the extent that the offset is possible not only in one direction, but with orientations over the entire circumference of the axis of the tool device.

This object is accomplished according to the present invention in a surgical tool device of this class by the guiding part being able to connected axially with the endoscope.

The guiding part can therefore be connected rigidly with the endoscope especially in one working configuration, but it can also be released again for insertion and removal. A circumferential groove is provided in a preferred embodiment at the proximal end of the endoscope and a movably mounted projection formed on the guiding part is provided for meshing with the circumferential groove. The projection is formed at the distal end of a rocker-like catch and/or the projection and can be pressed into the circumferential groove under the action of a transition part of the guide cannula to fix the endoscope and deflector axially when the circumferential groove of the endoscope and the projection of the guiding part are arranged in agreement with one another. On the one hand, a secure connection and, on the other hand, a connection that can be easily established and also easily released, is created by the present invention between the endoscope and the working tool comprising at least the guiding part and the tool part. It is thus ensured, in particular, that when the tool head of the tool part is led distally out of the jacket area of the guiding part, which jacket area at first surrounds it fully, there is a secure connection between the endoscope and the guiding part, which can be released, in a simple manner, only when the tool head is retracted into the jacket of the guiding part surrounding it.

Due to the variant of the tool device according to the present invention with a deflector, which has a laterally bent-off guiding surface in the distal end area thereof and is formed with a rotationally driven tool part, which is likewise designed flexibly in the distal end area thereof, directly proximally in front of the tool or tool head proper, the tool part is bent off to the side at the flexible end area thereof when being pushed in through the deflector and the tool head is thus brought out of alignment with the axis of the deflector and tool part, so that the desired and intended task in a direction offset from the axis or task out of alignment with the axis is possible as a result.

Provisions are made in a variant for the tool part to have a coil directly proximally from the tool in its distal end area.

A guiding cannula, which receives the tool part and is mounted with the tool part within the guiding part, may be provided in a preferred embodiment.

If it is desired or necessary, as in the embodiment of the guiding part as a bent-off deflector, to bring the deflector, guiding part and guiding cannula of the tool part into a suitable rigid circumferential alignment with one another, provisions are made in a preferred embodiment for the guiding cannula to have proximally an axially parallel outer groove and for the guiding part to have, within a proximal connection part, a pin directed axially parallel for cooperation with the groove, wherein especially a tube of the guiding part is axially movable relative to its coupling part against the action of a spring.

Provisions are made in further preferred embodiments of the present invention for the guiding cannula and the tool part to be connected with one another axially rigidly but rotatably relative to one another and/or for the tool part to be able to be coupled with the driven shaft of a rotating drive.

As was suggested above, provisions may be made, in particular, for the guiding part to be designed as a deflector with a guiding section bent off laterally at its distal end in relation to its axis. Provisions are now made in a variant for both the guiding cannula and the tool part to be made flexible in their distal end area.

The guiding cannula is preferably provided in its distal end area with slots extending over only part of the circumference, with the slots extending over 200° to 300°. The flexibility of the guiding cannula is likewise made possible here in the end area thereof in a simple manner.

Since the flexibility of the guiding cannula is not isotropic but can be preferably bent in one direction in its end area in which the slots are located (or also in the opposite direction) especially in the embodiment of the above concrete embodiment, it is necessary to bring the deflector and the guiding cannula [into] a rigid circumferential orientation in relation to one another in the above-described manner, i.e., especially such that the slots are arranged on the side of the cannula that is located opposite the guiding surface of the deflector.

On the whole, the present invention creates a surgical tool device with which the surgeon can perform necessary tasks, especially cutting resection tasks on bone material, such as vertebrae, or tissue resection in the region of vertebrae in a simple and reliable manner.

Further advantages and features of the present invention appear from the claims and from the following description, in which an exemplary embodiment of the present invention is explained specifically with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a longitudinal sectional view through a preferred embodiment of the tool unit according to the present invention according to A-A in FIG. 2;

FIG. 2 is a top view of the device according to the present invention according to FIG. 1 in the direction of arrow II;

FIG. 3 is a side view of a guiding part in the form of a deflector of the tool unit according to the present invention;

FIG. 4 is a longitudinal sectional view showing the deflector with the proximal connecting part;

FIG. 5 is an exploded view of the deflector according to FIGS. 3 and 4;

FIG. 6 is a juxtaposed view of a guiding cannula and a tool part with shaft and tool of the tool unit according to the present invention;

FIG. 7 is an enlarged partially cut away side view of the guiding cannula;

FIG. 10 is a longitudinal sectional view, through a tool unit according to the present invention, showing together with the view in FIG. 1, another part of the sequence in which the tool according to the present invention is made ready for use; and FIG. 11 is a longitudinal sectional view, through a tool unit according to the present invention, showing together with the view in FIG. 1, another part of the sequence in which the tool according to the present invention is made ready for use.

DESCRIPTION OF THE PREFERRED EMBODIMENTS

Figure 8:
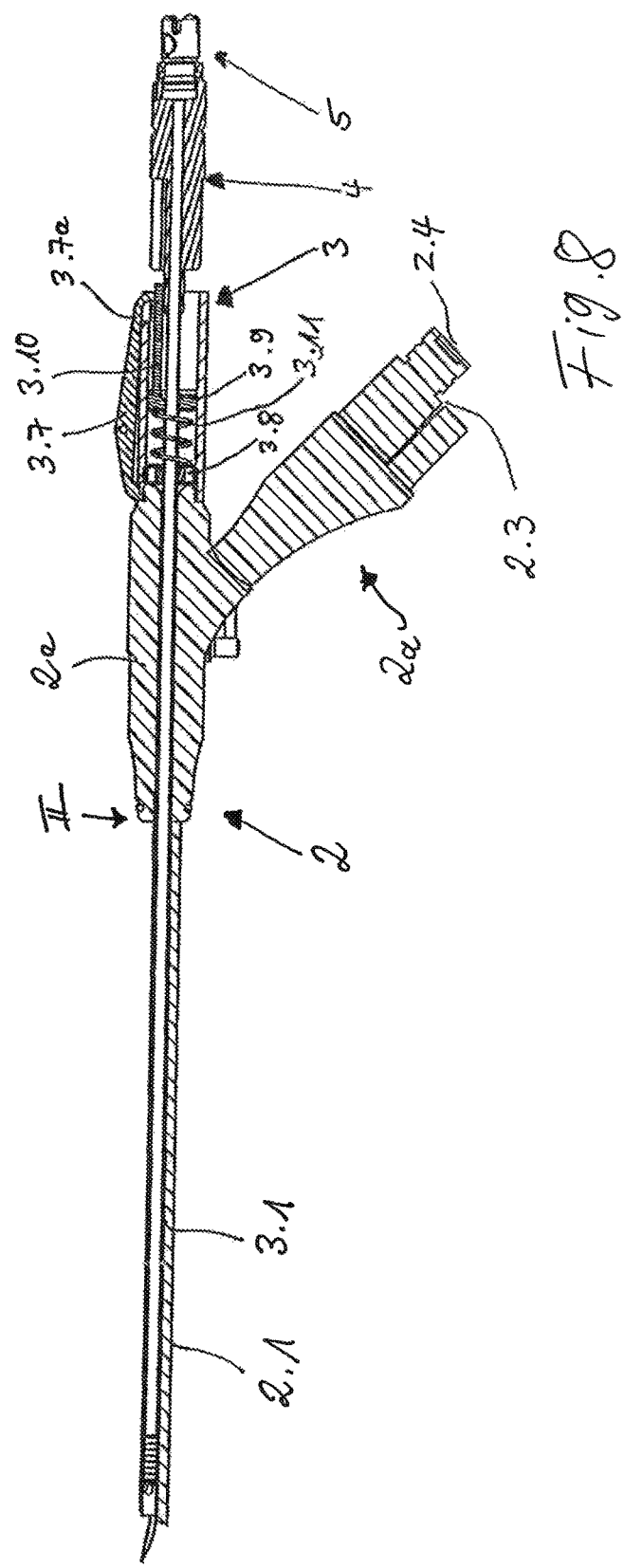
FIG. 8 is a longitudinal sectional view, through a tool unit according to the present invention, showing together with the view in FIG. 1, one part of the sequence in which the tool according to the present invention is made ready for use.

Referring to the drawings in particular, in the embodiment shown, the surgical tool device 1 according to the present invention has an endoscope 2, a guiding part 3 in the form of a deflector 3, a guiding cannula 4 and a tool part 5.

The endoscope 2 has a stretched working channel 2.1 with a proximal opening 2.2 aligned therewith for inserting tools. The endoscope 2 has, furthermore, not shown here more specifically, a bent illuminating inlet 2.3 and an observation outlet 2.4 extending in parallel hereto, which are in connection with corresponding channels transparent to light, wherein an illuminating unit may be connected to the former and an observation unit, for example, a camera, can be connected to the latter, and a screen can be connected via these. Finally, rinsing inlets and rinsing outlets 2.5, 2.6 are provided, at least one of which and optionally also both may be directly in connection with the working channel during intermittent rinsing and suction. An endoscope usually has, besides the working channel, as was already suggested, further channels, for example, for optical transmission and/or for rinsing, which are not shown specifically in the figures for clarity's sake, because these are not specifically relevant to the subject of the present invention.

A deflector tube 3.1 of the guiding part 3 is arranged in the working channel 2.1 of the endoscope 2. The deflector tube 3.1 has a distal opening 3.2. Extending beyond this, it has a one-sided guiding section 3.3, which is slightly bent in relation to the axis X of the deflector tube 3.1 or of the guiding part 3.3 with an essentially axial extension, which reaches from a wall side of the deflector tube 3.1 laterally in an arc-shaped pattern to a radial position, which is approximately aligned with the side of the deflector tube 3.1 located diagonally opposite the outlet side of the guiding section 3.3. Section 3.3 has a spoon-shaped design.

A connecting part 3.5 of the guiding tube 3 has a cylindrical jacket 3.6, which acts as a catch holder for a rocker-like catch 3.7, by means of which the deflector 3 can be securely fixed to the endoscope 2. A bushing 3.8 is fixed at the distal end of the cylindrical jacket 3.6 in the interior thereof, for example, by bonding, welding or screwing in; it may also be made in one piece with the jacket 3.6.

The deflector tube 3.1 is passed slidingly through the bushing 3.8 and is rigidly connected, on the one hand, with a ring washer 3.9. On its side facing away from the deflector tube 3.1, the ring washer 3.9 has, furthermore, a pin 3.10, which extends radially offset but in parallel to the axis X and whose function will be explained below.

A coil spring 3.11 is arranged between the bushing 3.8 and the ring washer 3.9, and a (plain) washer each, made of metal, preferably stainless steel, which material may also be that of the spring 3.11, is arranged between the spring 3.11 and the respective bushing 3.8 as well as the ring washer 3.9.

The deflector tube 3.1 can be correspondingly displaced against the action of the spring 3.11 in the distal direction and is displaced by the spring to a limited extent in the proximal direction upon release.

The guiding cannula 4 has, on the one hand, a metallic shaft 4.1 and, on the other hand, a transition part 4.2 (FIG. 6), which can be recognized more clearly in FIG. 7, at its proximal end.

Figure 9:
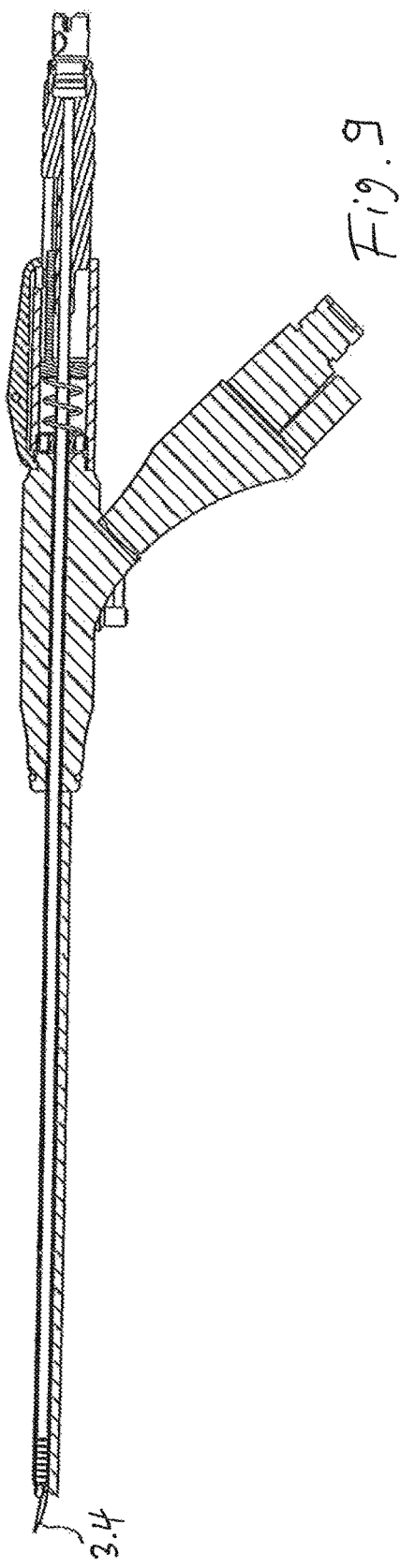
FIG. 9 is a longitudinal sectional view, through a tool unit according to the present invention, showing together with the view in FIG. 1, another part of the sequence in which the tool according to the present invention is made ready for use.

The distal end area of the shaft 4.1 is provided on one side with a plurality of slots 4.3, which are located in parallel radial planes and extend over more than half the circumference of the shaft, i.e., over about 200° to 270°. The end area of the shaft 4.1 can be bent as a result towards the side of the slots (FIGS. 9 and 10).

Since bending in the direction predetermined by the course of the bent, spoon-shaped end area of the deflector 3 must be guaranteed, it must be ensured that the guiding cannula 4 is seated in the correct orientation in the deflector tube 3.1.

This purpose is served, on the one hand, by the above-mentioned pin 3.10 of the deflector 3 and, on the other hand, by an axially parallel longitudinal groove 4.4, which is formed on the transition part 4.2 of the guiding tube 4, and with which the pin 3.10 meshes when the shaft 4.1 is pushed into the deflector tube 3.1 and the transition part 4.2 is pushed into the jacket 3.6 of the guiding part 3, so that the guiding cannula 4 can only be pushed into the deflector 3 in the angular orientation determined hereby.

Further, FIG. 6 shows the tool part 5 with an essentially rigid tool shaft 5.1, with a proximal coupling part 5.2 and with a tool 5.3, as a cutting head, but other tools to be used in a rotational manner may be used as well.

The tool shaft 5.1 is likewise made flexible in its distal end area, namely, due to a coil 5.4, which is only suggested in the drawing, especially in the form of a coil spring, in which the individual turns are directly in contact with one another.

To use the tool unit according to the present invention, the tool part 5 with the tool shaft 5.1 is pushed into the guiding tube 4, as it is shown, for example, in FIG. 1, and the tool 5.3 proper projects distally over the distal end of the shaft 4.1 of the guiding tube 4, i.e., it protrudes from the shaft 4.1. The tool part 5 and the guiding tube 4 are connected with one another axially, but in such a way that they rotate in unison, optionally directly via a radial pin (not shown), which is fixed via a transition part 4.2 protruding into an annular groove at the distal end of the coupling part 5.2. The tool part 5 and the guiding tube 4 are coupled with one another in this position axially rigidly but rotatably relative to one another in the proximal area of the parts 4.2, 5.2. The coupling may also be brought about, in particular, via a handle, which has a rotary drive and is connected axially—and rotating in unison—with the connecting part 4.2 of the guiding tube 4 by means of a locking connection in a manner that is not shown, while the coupling 5.2 of the tool part 5 is also connected axially with the tool shaft of the drive in the handle via the connection of the connecting part 4.2 with the handle in such a way that they rotate in unison.

To connect the endoscope 2 and the deflector tube 3.1, the latter is at first pushed into the endoscope 2 to the extent that the projection 3.13 of the catch 3.7 reaches at the deflector 3 an axial position that agrees with that of the circumferential groove 2.7 on a contact part 2a of the endoscope. A proximal projection 3.7a of the catch 3.7 is broader than the groove 4.4, so that as soon as the catch 3.7 is pushed with its proximal projection 3.7a over the transition part 4.2, the proximal projection 3.7a of the catch 3.7 is raised radially or pressed outwardly by the circumferential surface of the transition part 4.2 and the distal projection 3.13 of the catch 3.7 is thus pressed into the groove 2.7 on the grip part 2.5 of the endoscope 2 (transition from FIG. 8 to FIG. 9), so that the two are thus coupled rigidly axially (FIG. 9).

The tool unit according to the present invention is preferably used to process, such as cut out bone material on vertebrae of the spine. After the minimally invasive preparation of an insertion path and insertion of the endoscope to the work area at the corresponding bone, especially vertebra, the deflector 3 is pushed in at first with the deflector tube 3.1 with the guiding tube 4 pushed in completely, but without tensioning the spring 3.11, for example, starting from the relative positions shown in FIG. 1 to the relative positions of the parts as shown in FIG. 8.

The guiding tube 4 is then advanced until the transition part 4.2 comes in contact with the ring washer 3.9, likewise still without tensioning the spring 3.11, as this is shown in FIG. 9. The deflector tube 3.1 now remains up to its distal opening 2.2 within the endoscope 2.

By contrast, both the guiding tube 4 with the flexible end area provided with the slots 4.3 and the tool part 5 with its end area, which is flexible due to the coil 5.4, project. Both flexible end areas will come to lie in the spoon-like guiding section 3.3 of the deflector 3 and are bent to the side by the deflector and with it the tool 5.3 as well, which also projects distally over the tip 3.4 of the spoon-like guiding section 3.3 of the deflector 3. As a result, the tool 5.3 can operate freely and prepare, for example, a flute in the bone material of a vertebral after the rotary drive is switched on.

An axial feed and thus an axial roughing of the tool is brought about by moving the tool part 5 with the guiding tube 4 against the spring action relative to the endoscope 2 while compressing the spring 3.11 in the distal direction via the handle of the drive (transition from FIG. 9 to FIG. 10), while the deflector 3.1 is also carried via the ring washer 3.9.

After the end of the task, the guiding part 3 designed as a deflector is again released from the endoscope 2 at the transition from FIG. 9 to FIG. 8 by the transition part 4.2 of the guiding cannula releasing again the proximal projection 3.7a of the catch 3.7 when said guiding cannula is pulled out, so that the distal projection 3.13 can again be released from the circumferential groove 2.7 of the endoscope 2 and the endoscope 2 and the guiding part 3 (deflector) can thus be separated.

Individual embodiments or individual features shown in the above description and also in the drawings may be essential for the embodiment of the present invention not only in connection with other individual embodiments, but also in themselves without a necessary connection with other individual features or individual embodiments described in their linguistic context.

While specific embodiments of the invention have been shown and described in detail to illustrate the application of the principles of the invention, it will be understood that the invention may be embodied otherwise without departing from such principles.

What is claimed is:

1. A surgical tool device comprising:
   a guiding part;
   a tool part;
   an endoscope with a working channel through which the guiding part and the tool part, guided in the same, are moveable with distal ends thereof to a distal working area, wherein the tool part has a tool shaft with a rotary tool, and the guiding part is rigidly connectable with the endoscope axially, whereby when connected, there is no relative movement in an axial direction; and
   a guiding cannula that receives the tool part and is receivable with the tool part, within the guiding part and wherein the guiding part comprises a deflector with a guiding section bent to a side in relation to a deflector axis at a deflector distal end and wherein both the guiding cannula has a flexible distal end area and the tool part has a flexible distal end area, wherein the guiding cannula has an axially parallel outer groove proximally and the guiding part has a pin directly axially parallel within a proximal connecting part for cooperating with the groove.

2. A device in accordance with claim 1, wherein the endoscope has a circumferential groove at the proximal end of the endoscope and the guiding part has a movably mounted projection formed on the guiding part for meshing with the circumferential groove.

3. A device in accordance with claim 2, wherein the projection is formed at the distal end of a rocker catch.

4. A device in accordance with claim 3, wherein in case of an axially agreeing arrangement of the circumferential groove of the endoscope and of the projection of the guiding part, the projection is pressable into the circumferential groove under the action of a transition part of the guiding cannula for fixing the endoscope and the deflector axially.

5. A device in accordance with claim 1, wherein the guiding cannula and the tool part are connected to one another axially rigidly but rotatably relative to one another.

6. A device in accordance with claim 2, wherein the guiding cannula and the tool part are connected to one another axially rigidly but rotatably relative to one another.

7. A device in accordance with claim 1, wherein the guiding part and the guiding cannula are connectable with one another in such a way that they rotate in unison.

8. A device in accordance with claim 2, wherein the guiding part and the guiding cannula are connectable with one another in such a way that they rotate in unison.

9. A device in accordance with claim 1, further comprising a spring wherein the tool part has a coupling part and the guiding part has a tube that is axially movable relative to the coupling part against an action of the spring.

10. A device in accordance with claim 2, further comprising a spring wherein the tool part has a coupling part and the guiding part has a tube that is axially movable relative to the coupling part against an action of the spring.

11. A device in accordance with claim 1, wherein the tool part is coupleable with the driven shaft of a rotating drive.

12. A device in accordance with claim 2, wherein the tool part is coupleable with the driven shaft of a rotating drive.

13. A surgical tool device comprising:
   an endoscope with a working channel;
   a guiding part received in the working channel, the guiding part being moveable in the working channel to move a distal end to a distal working area, the guiding part including a connecting part for connecting and disconnecting the guiding part from the endoscope to releaseably fix the guiding part in an axial position with respect to the working channel; and
   a tool part guided in the guiding part, wherein the tool part has a tool shaft with a rotary tool further comprising a guiding cannula, which receives the tool part and which is receivable, with the tool part, within the guiding part and wherein the guiding part comprises a deflector with a guiding section bent to a side in relation to a deflector axis at a deflector distal end and wherein both the guiding cannula has a flexible distal end area and the tool part has a flexible distal end area, wherein the guiding cannula has an axially parallel outer groove proximally and the guiding part has a pin directly axially parallel within a proximal connecting part for cooperating with the groove.

14. A device in accordance with claim 13, wherein the endoscope has a circumferential groove at a proximal end of the endoscope and the guiding part comprises a movably mounted projection formed on the guiding part for engaging with the circumferential groove.

15. A device in accordance with claim 14, wherein in case of an axially agreeing arrangement of the circumferential groove of the endoscope and of the projection of the guiding part, the projection is pressable into the circumferential groove under the action of a transition part of the guiding cannula for fixing the endoscope and the deflector axially.

16. A device in accordance with claim 13, wherein the guiding cannula and the tool part are connected to one another axially rigidly but rotatably relative to one another.

17. A device in accordance with claim 14, wherein the guiding cannula and the tool part are connected to one another axially rigidly but rotatably relative to one another.

18. A device in accordance with claim 13, wherein the guiding part and the guiding cannula are connectable with one another in such a way that they rotate in unison.

19. A device in accordance with claim 14, wherein the guiding part and the guiding cannula are connectable with one another in such a way that they rotate in unison.

20. A device in accordance with claim 13, further comprising a spring wherein the tool part has a coupling part and the guiding part has a tube that is axially movable relative to the coupling part against the action of the spring.

21. A device in accordance with claim 14, further comprising a spring wherein the tool part has a coupling part and the guiding part has a tube that is axially movable relative to the coupling part against the action of the spring.

\* \* \* \* \*